US012595268B2

(12) United States Patent
Kim et al.

(10) Patent No.: US 12,595,268 B2
(45) Date of Patent: Apr. 7, 2026

(54) ACID ANHYDRIDE COMPOUND, AND POLYAMIDEIMIDE RESIN AND FILM USING THE SAME

(71) Applicant: KOREA ADVANCED INSTITUTE OF SCIENCE AND TECHNOLOGY, Daejeon (KR)

(72) Inventors: Sang Youl Kim, Daejeon (KR); Seong Jong Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 191 days.

(21) Appl. No.: 18/517,326

(22) Filed: Nov. 22, 2023

(65) Prior Publication Data

US 2024/0262843 A1 Aug. 8, 2024

(30) Foreign Application Priority Data

Jan. 25, 2023 (KR) ........................ 10-2023-0009443

(51) Int. Cl.
*C07D 493/04* (2006.01)
*C08G 73/14* (2006.01)
*C08J 5/18* (2006.01)

(52) U.S. Cl.
CPC ........... *C07D 493/04* (2013.01); *C08G 73/14* (2013.01); *C08J 5/18* (2013.01); *C08J 2379/08* (2013.01)

(58) Field of Classification Search
CPC .............................. C07D 493/04; C08G 73/14
See application file for complete search history.

(56) References Cited

FOREIGN PATENT DOCUMENTS

| | | | |
|---|---|---|---|
| JP | 2023109720 | A | 8/2023 |
| KR | 20140085064 | A | 7/2014 |

OTHER PUBLICATIONS

Machine translation of JP 2023-109720. Retrieved Jul. 30, 2025.*
Action in JP 2023-195696 issued on Nov. 27, 2024 (2 pgs).
Seong Jong Kim, et al.; "Old Materials for New Technology: Transparent Polyimides with High Tg and Low CTE"; Department of Chemistry, KAIST, Daejeon 34141, Korea; https://news.samsung.com/uk/experts-predict-aquatichighways-air-taxis-and-space-hotels-for-life-in-50-years-time; Aug. 29, 2019 (36 pgs.).

* cited by examiner

*Primary Examiner* — Prashant J Khatri
(74) *Attorney, Agent, or Firm* — NIXON PEABODY LLP

(57) ABSTRACT

Provided are an acid anhydride compound having a novel structure, and a polyamideimide resin and a polyamideimide film produced therefrom. Specifically, since the polyamide-imide film according to the present invention includes a structural unit derived from the acid anhydride compound, it may have high thermal resistance and a low coefficient of thermal expansion while being colorless and transparent.

11 Claims, 6 Drawing Sheets

ACID ANHYDRIDE COMPOUND, AND POLYAMIDEIMIDE RESIN AND FILM USING THE SAME

CROSS-REFERENCE TO RELATED APPLICATIONS

This application claims priority under 35 U.S.C. § 119 to Korean Patent Application No. 10-2023-0009443, filed on Jan. 25, 2023, in the Korean Intellectual Property Office, the disclosure of which is incorporated herein by reference in its entirety.

TECHNICAL FIELD

The present disclosure relates to an acid anhydride compound having a novel structure, and a polyamideimide resin and a polyamideimide film produced therefrom.

BACKGROUND

Recently, as display devices have advanced in various forms, it has become important to be lighter, slimmer, and more flexible, and attempts to replace a conventional glass substrate with a polyimide-based film which is light and flexible and has excellent chemical resistance and the like are continuing. However, in order to apply the polyimide-based film to a display device, it is essential to improve its inherent yellow index properties and impart colorless and transparent optical properties.

Furthermore, since a flexible device involves a high temperature process such as those in thin film transistor (TFT) and organic matter deposition, it requires excellent thermal dimensional stability for being not deformed even in a high temperature process and minimizing a difference in expansion and contraction between different types of materials in a high temperature process. As an example, it requires thermal properties such as a low coefficient of thermal expansion of 20 ppm/° C.; or less and a high glass transition temperature of 400° C.; or higher, which are similar to those of inorganic matter and metal used in TFT.

However, since the optical properties and thermal resistance of the polyimide-based film are in a trade-off relationship, when a colorless and transparent optical properties are imparted to the polyimide-based film, the thermal resistance is decreased and the coefficient of thermal expansion is increased. Thus, studies for developing a polyimide-based film which is colorless and transparent while having high thermal resistance and a low coefficient of thermal expansion are continuing, but there are limitations in satisfying all of them.

RELATED ART DOCUMENTS

Patent Documents

Korean Patent Laid-Open Publication No. 10-2014-0085064 A (Jul. 7, 2014)

SUMMARY

An embodiment of the present invention is directed to providing an acid anhydride compound having a novel structure, which is a monomer allowing production of a highly heat-resistant, colorless, and transparent polyimide-based film, and a method of producing the same.

Another embodiment of the present invention is directed to providing a polyamideimide resin and a polyamideimide film including a structural unit derived from the novel acid anhydride compound.

Still another embodiment of the present invention is directed to providing a flexible display element including the polyamideimide film.

In one general aspect, an acid anhydride compound represented by the following Chemical Formula 1 is provided:

[Chemical Formula 1]

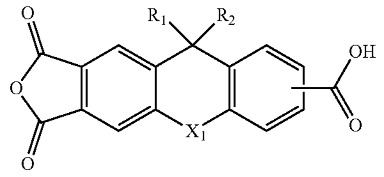

wherein $R_1$ and $R_2$ are independently of each other hydrogen, (C1-C20)alkyl, fluoro(C1-C20)alkyl, (C6-C20)aryl, or (C3-C20)heteroaryl, and at least one of the $R_1$ and $R_2$ is fluoro(C1-C20)alkyl, (C6-C20)aryl, or (C3-C20)heteroaryl; and $X_1$ is O or $SO_2$.

The acid anhydride compound according to an exemplary embodiment may be represented by the following Chemical Formula 2:

[Chemical Formula 2]

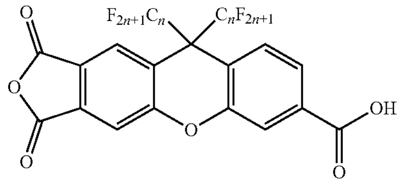

wherein n is an integer of 1 to 5.

The acid anhydride compound according to an exemplary embodiment may be represented by the following Chemical Formula 3:

[Chemical Formula 3]

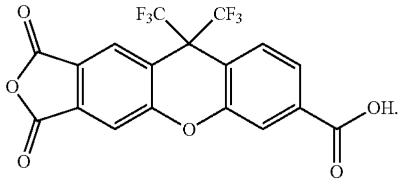

In another general aspect, a polyamideimide includes: a structural unit derived from an acid anhydride compound represented by the following Chemical Formula 1 and a structural unit derived from an aromatic diamine:

[Chemical Formula 1]

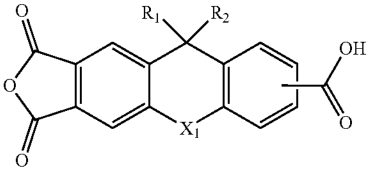

wherein $R_1$, $R_2$, and $X_1$ are as defined above.

The polyamideimide according to an exemplary embodiment may include a repeating unit represented by the following Chemical Formula 5:

wherein $Ar_1$ and $Ar_2$ are independently of each other

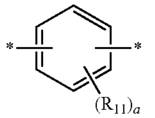

or

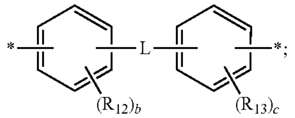

;

L is a single bond, —O—, —S—, or —$CR_{14}R_{15}$—;

$R_{11}$ to $R_{15}$ are independently of one another (C1-C3)alkyl or fluoro(C1-C3)alkyl; and a to c are independently of one another an integer of 0 to 2.

[Chemical Formula 5]

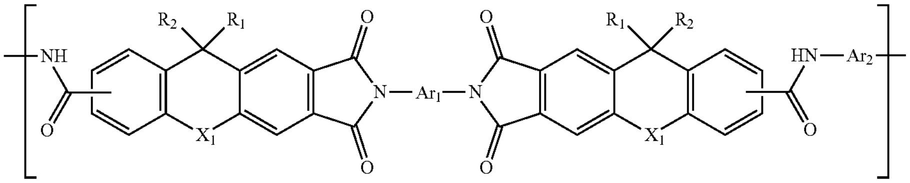

wherein $R_1$ and $R_2$ are independently of each other hydrogen, (C1-C20)alkyl, fluoro(C1-C20)alkyl, (C6-C20)aryl, or (C3-C20)heteroaryl, and at least one of the $R_1$ and $R_2$ is fluoro(C1-C20)alkyl, (C6-C20)aryl, or (C3-C20)heteroaryl;

$X_1$ is O or $SO_2$;

$Ar_1$ and $Ar_2$ are independently of each other

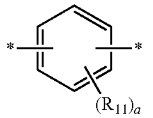

or

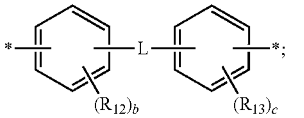

;

L is a single bond, —O—, —S—, —$SO_2$—, (C1-C7) alkylene, (C6-C12)arylene, or a combination thereof, and the arylene and the alkylene of L may be further substituted by one or more selected from (C1-C7)alkyl and halo(C1-C7)alkyl;

$R_{11}$ to $R_{13}$ are independently of one another (C1-C7)alkyl, (C1-C7)alkoxy, or halo(C1-C7)alkyl; and a to c are independently of one another an integer of 0 to 2.

The polyamideimide according to an exemplary embodiment may include a repeating unit represented by the following Chemical Formula 6:

$Ar_1$ and $Ar_2$ may be independently of each other selected from the following structures:

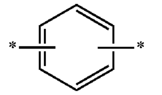

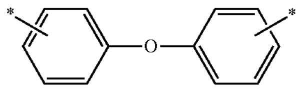

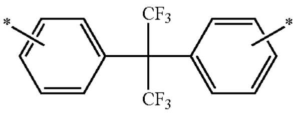

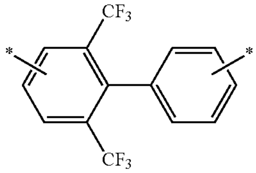

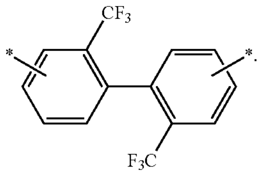

.

The polyamideimide according to an exemplary embodiment may include a repeating unit represented by the following Chemical Formula 7 or Chemical Formula 8:

[Chemical Formula 6]

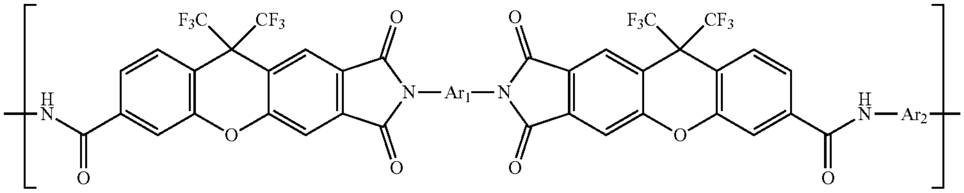

[Chemical Formula 7]

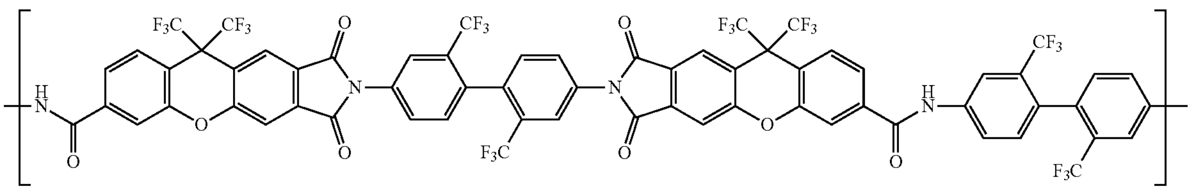

[Chemical Formula 8]

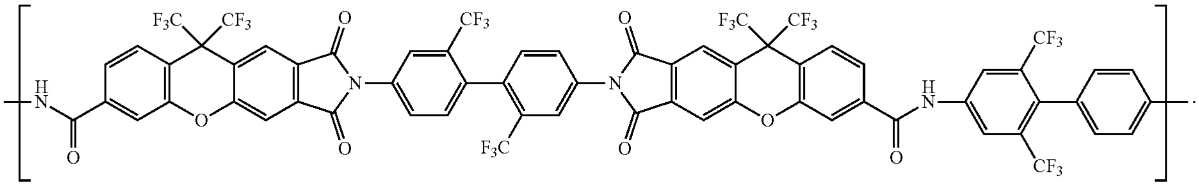

The polyamideimide may have a number average molecular weight of 10,000 to 200,000 g/mol.

In another general aspect, a method of producing a polyamideimide includes: reacting and imidizing an acid anhydride compound represented by the following Chemical Formula 1 and an aromatic diamine represented by the following Chemical Formula A to produce a dicarboxylic acid compound represented by the following Chemical Formula 4; and reacting the dicarboxylic acid compound represented by Chemical Formula 4 and an aromatic diamine represented by the following Chemical Formula B to produce a polyamideimide including a repeating unit represented by the following Chemical Formula 5:

In another general aspect, a polyamideimide film formed from the composition for forming a polyamideimide film is provided.

The polyamideimide film according to an exemplary embodiment may have a thickness of 1 to 20 μm and a glass transition temperature ($T_g$) of 400° C.; or higher.

The polyamideimide film according to an exemplary embodiment may have a coefficient of thermal expansion (CTE) of 20 ppm/° C.; or less as measured in a temperature range of 100 to 450° C.; by a thermomechanical analysis (TMA) method.

[Chemical Formula 1]

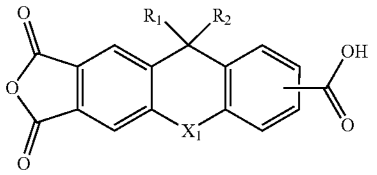

[Chemical Formula 4]

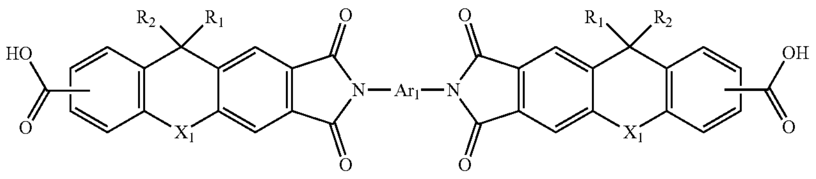

[Chemical Formula 5]

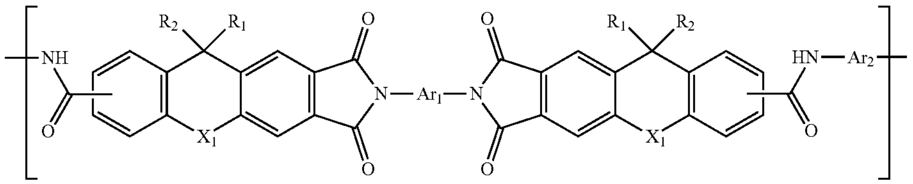

[Chemical Formula A]

$H_2N—Ar_1—NH_2$

[Chemical Formula B]

$H_2N—Ar_2—NH_2$ wherein $R_1$, $R_2$, $X_1$, $Ar_1$, and $Ar_2$ are as defined above in Chemical Formula 5.

In another general aspect, a composition for forming a polyamideimide film includes the polyamideimide.

The polyamideimide according to an exemplary embodiment may have a yellow index in accordance with ASTM D1925 of 4 or less.

In another general aspect, a flexible display panel includes the polyamideimide film.

In still another general aspect, a dicarboxylic acid compound represented by the following Chemical Formula 4 is provided:

[Chemical Formula 4]

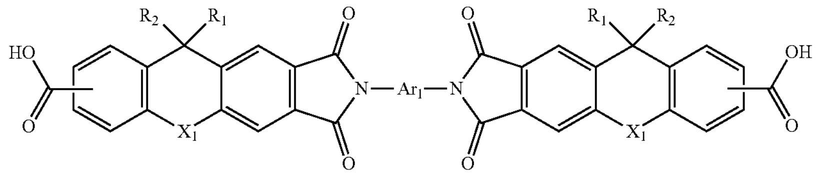

wherein $R_1$, $R_2$, $X_1$, and $Ar_1$ are as defined above in Chemical Formula 5.

Other features and aspects will be apparent from the following detailed description, the drawings, and the claims.

DETAILED DESCRIPTION OF EMBODIMENTS

Figure 1:
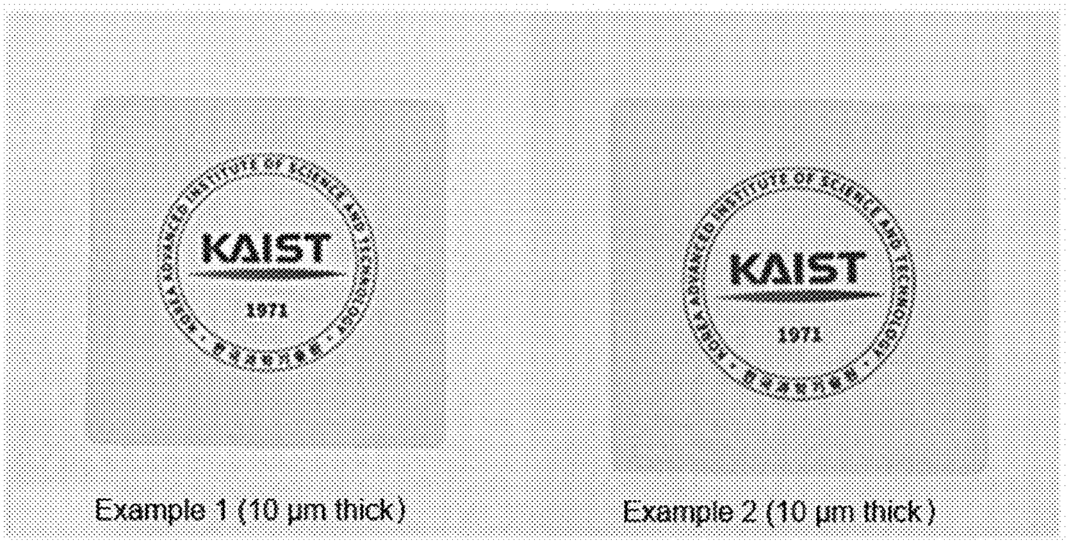
FIG. 1 is photographs of polyamideimide films produced in Examples 1 and 2.
Figure 2:
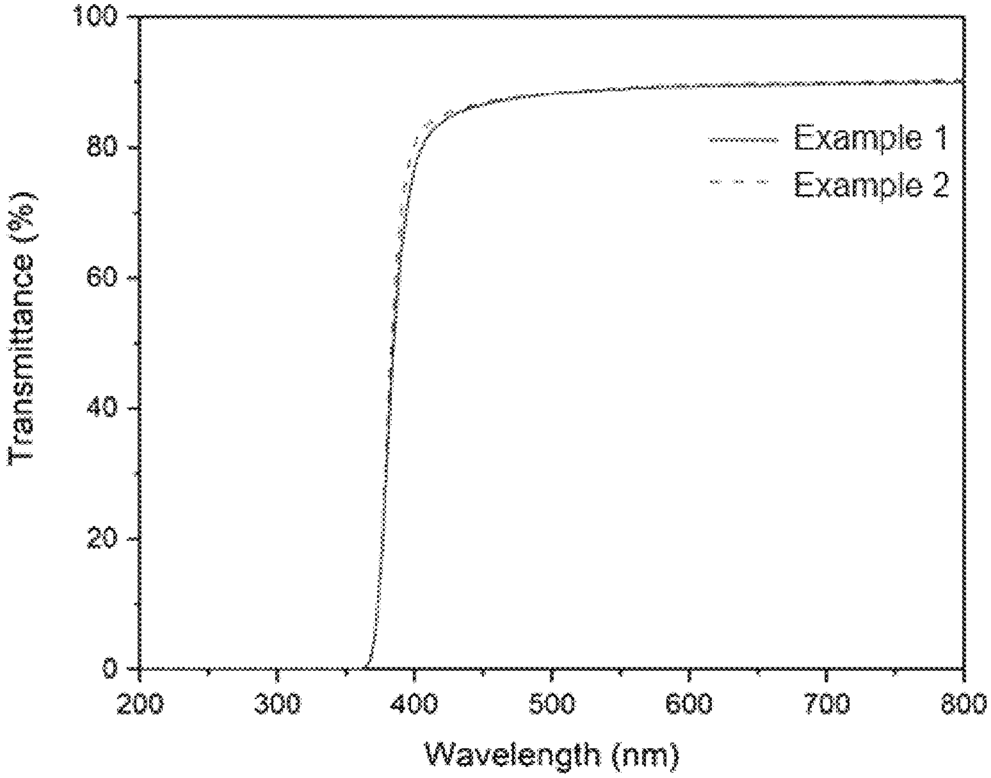
FIG. 2 is a transmittance graph in an ultraviolet-visible region of the polyamideimide films produced in Examples 1 and 2.
Figure 3:
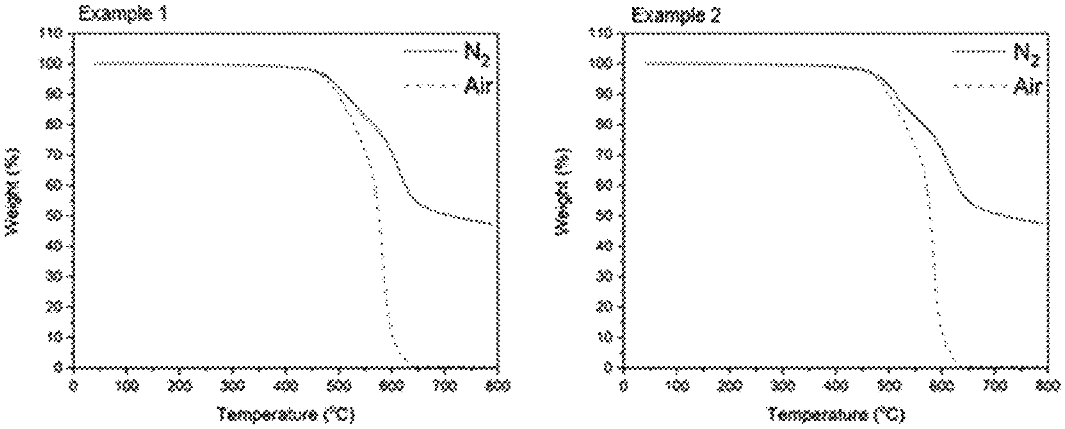
FIG. 3 is thermogravimetric analysis graphs in a nitrogen ($N_2$) environment and an air (air) environment of the polyamideimide films produced in Examples 1 and 2.
Figure 4:
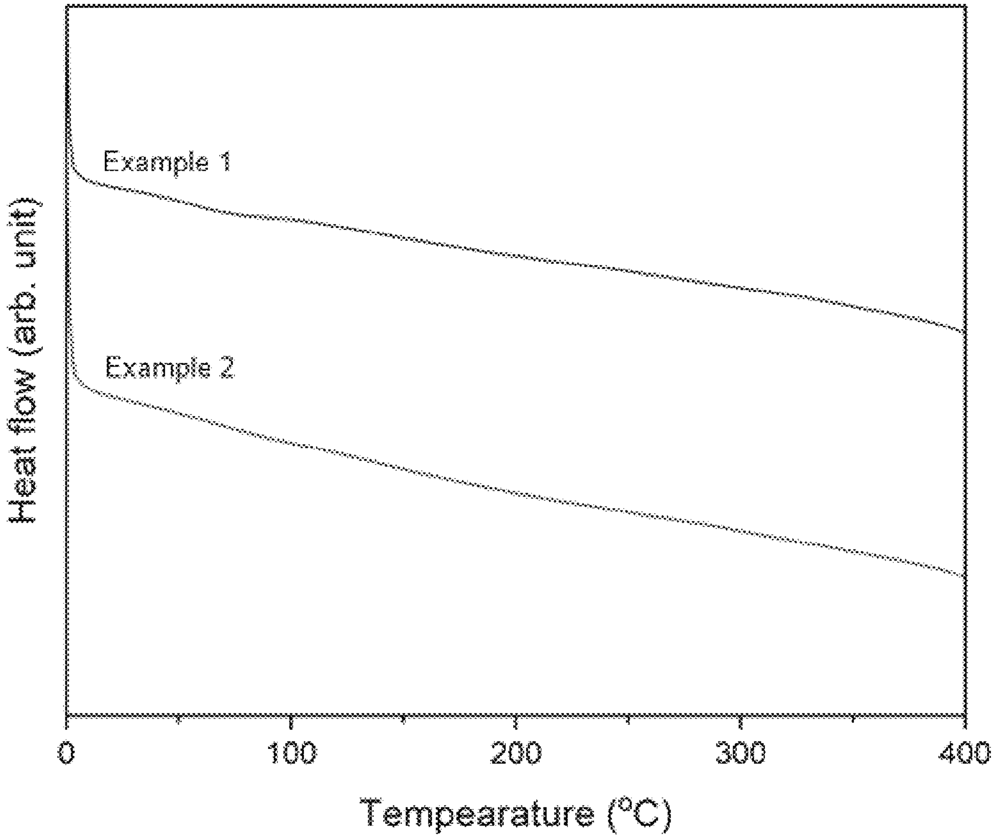
FIG. 4 is a differential scanning calorimetry analysis graph of the polyamideimide films produced in Examples 1 and 2.
Figure 5:
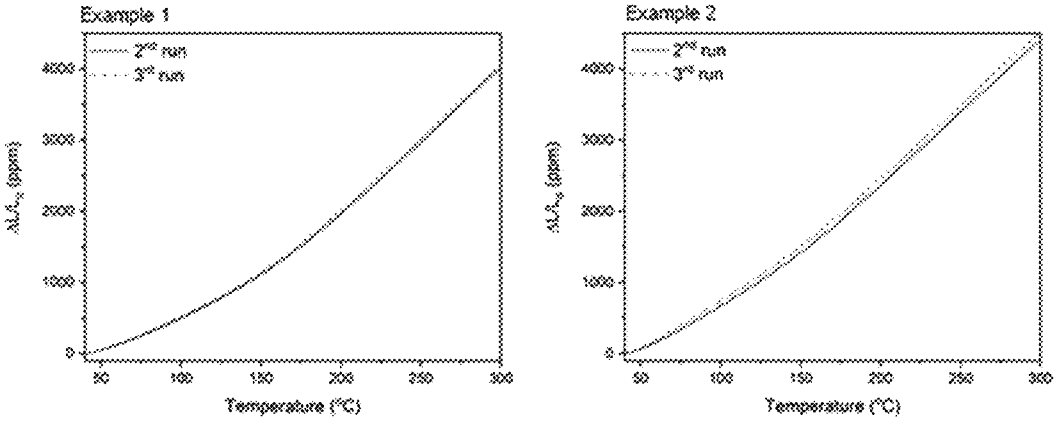
FIG. 5 is a thermomechanical analysis graph of the polyamideimide films produced in Examples 1 and 2.
Figure 6:
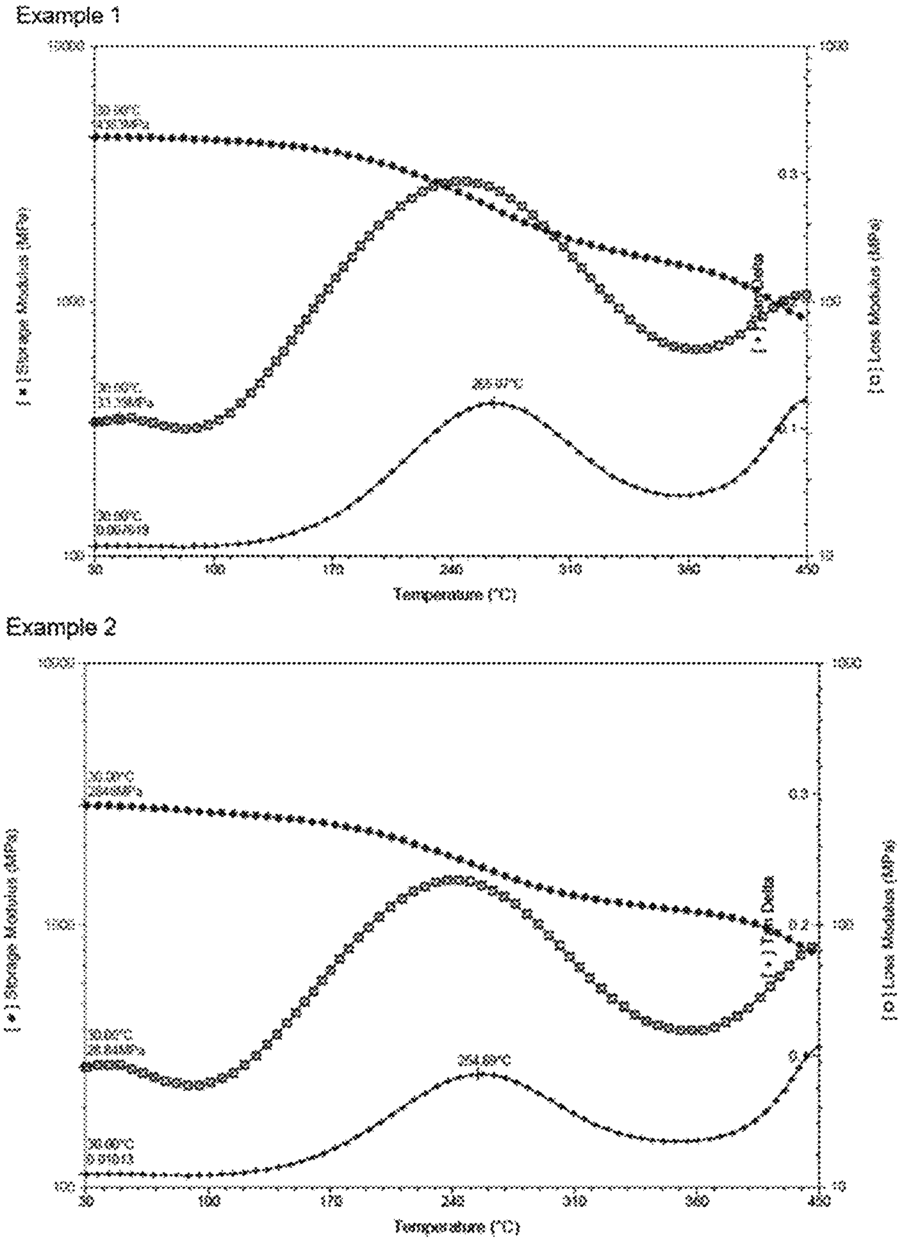
FIG. 6 is dynamic mechanical analysis graphs of the polyamideimide films produced in Examples 1 and 2.

In the present specification, unless otherwise defined, all technical terms and scientific terms have the same meanings as those commonly understood by a person skilled in the art to which the present invention pertains. The terms used herein are only for effectively describing a certain specific example, and are not intended to limit the present invention.

The singular form used in the present specification may be intended to also include a plural form, unless otherwise indicated in the context.

In addition, the numerical range used in the present specification includes all values within the range including the lower limit and the upper limit, increments logically derived in a form and span of a defined range, all double limited values, and all possible combinations of the upper limit and the lower limit in the numerical range defined in different forms. Unless otherwise defined in the present specification, values which may be outside a numerical range due to experimental error or rounding off of a value are also included in the defined numerical range.

The term "comprise" in the present specification is an open-ended description having a meaning equivalent to the term such as "is/are provided", "contain", "have", or "is/are characterized", and does not exclude elements, materials, or processes which are not further listed.

The term "alkyl" in the present specification is an organic radical derived from an aliphatic hydrocarbon by removal of one hydrogen, and may include both a straight chain and branched chain forms. The alkyl may have 1 to 20 carbon atoms, specifically 1 to 15 carbon atoms, specifically 1 to 10 carbon atoms, specifically 1 to 7 carbon atoms, or specifically 1 to 5 carbon atoms. The alkyl includes, as an example, methyl, ethyl, propyl, isopropyl, butyl, isobutyl, t-butyl, pentyl, hexyl, ethylhexyl, and the like, but is not limited thereto.

The term "fluoroalkyl" in the present invention means that at least one or more hydrogens in the alkyl are substituted with a fluoro group (−F).

The term "aryl" in the present specification refers to an organic radical derived from an aromatic hydrocarbon by removal of one hydrogen, and includes a monocyclic or fused cyclic system including suitably 4 to 7, preferably 5 or 6 ring atoms in each ring and includes even a form in which a plurality of aryls are linked by a single bond. As an example, aryl includes phenyl, naphthyl, biphenyl, terphenyl, and the like, but is not limited thereto.

The term "heteroaryl" in the present specification refers to a divalent organic radical derived by removal of one hydrogen from heteroaryl. The "heteroaryl" refers to an aryl group including at least one heteroatom selected from N, O, S, and Se as an aromatic ring skeleton atom and carbon as a remaining aromatic ring skeleton atom, is 5 or 6-membered monocyclic heteroaryl and a polycyclic heteroaryl fused with one or more benzene rings, and may be partially saturated. In addition, the heteroaryl in the present invention also includes a form in which one or more heteroaryls are linked by a single bond. As a specific example, it may include monocyclic heteroaryl such as furyl, thiopenyl, pyrrolyl, imidazolyl, pyrazolyl, thiazolyl, isothiazolyl, isoxazolyl, oxazolyl, triazinyl, pyridyl, pyrazinyl, pyrimidinyl, and pyridazinyl; polycyclic heteroaryl such as benzofuranyl, beizothiophenyl, isobenzofuranyl, benzoimidazolyl, benzothiazolyl, benzoisothiazolyl, benzoisoxazolyl, benzoxazolyl, isoindolyl, indolyl, indazolyl, quinolyl, isoquinolyl, dibenzofuranyl, dibenzothiophenyl, carbazolyl, and benzocarbazolyl; and the like, but is not limited thereto.

Hereinafter, the present invention will be described in detail.

An exemplary embodiment of the present invention provides an acid anhydride compound having a novel structure, which is a monomer allowing production of a highly heat-resistant, colorless, and transparent polyimide-based film.

Specifically, the acid anhydride compound according to an exemplary embodiment may be represented by the following Chemical Formula 1:

[Chemical Formula 1]

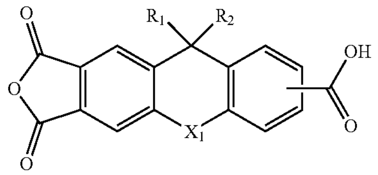

wherein $R_1$ and $R_2$ are independently of each other hydrogen, (C1-C20)alkyl, fluoro(C1-C20)alkyl, (C6-C20)aryl, or (C3-C20)heteroaryl, and at least one of the $R_1$ and $R_2$ is fluoro(C1-C20)alkyl, (C6-C20)aryl, or (C3-C20)heteroaryl; and $X_1$ is O or $SO_2$.

As an example, in Chemical Formula 1, $R_1$ and $R_2$ may be independently of each other hydrogen, (C1-C7)alkyl, fluoro (C1-C7)alkyl, (C6-C12)aryl, or (C3-C12)heteroaryl, and at least one of $R_1$ and $R_2$ may be fluoro (C1-C7)alkyl, (C6-C12)aryl, or (C3-C12)heteroaryl.

As an example, in Chemical Formula 1, $R_1$ and $R_2$ may be the same as or different from each other and be fluoro (C1-C20)alkyl, and specifically, may be perfluoro(C1-C20) alkyl or perfluoro(C1-C7)alkyl.

Specifically, the acid anhydride compound according to an exemplary embodiment may be represented by the following Chemical Formula 2:

[Chemical Formula 2]

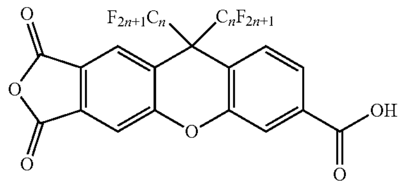

wherein n is an integer of 1 to 5.

As an example, in Chemical Formula 2, n may be an integer of 1 to 3, or 1 or 2.

More specifically, the acid anhydride compound according to an exemplary embodiment may be represented by the following Chemical Formula 3, but is not limited thereto:

[Chemical Formula 3]

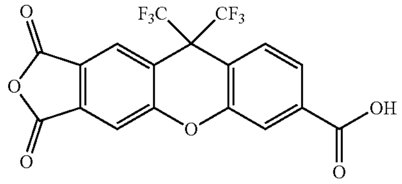

Another exemplary embodiment of the present invention provides a polyamideimide including: a structural unit derived from an acid anhydride compound represented by the following Chemical Formula 1:

[Chemical Formula 1]

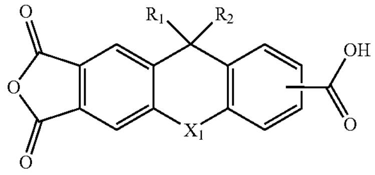

wherein $R_1$, $R_2$, and $X_1$ are as defined above.

That is, the acid anhydride compound according to an exemplary embodiment may be applied as a monomer for producing a polyamideimide polymer and may synthesize a polyamideimide by a reaction with a diamine compound.

Specifically, the polyamideimide according to an exemplary embodiment may include a structural unit derived from the acid anhydride compound represented by Chemical Formula 1 and a structural unit derived from an aromatic diamine adjacent to each other, and for example, may include a repeating unit represented by the following Chemical Formula 5:

[Chemical Formula 5]

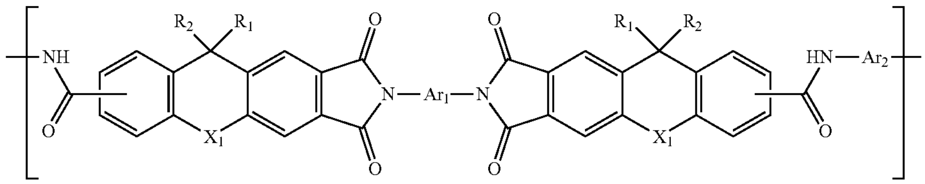

wherein $R_1$ and $R_2$ are independently of each other hydrogen, (C1-C20)alkyl, fluoro(C1-C20)alkyl, (C6-C20)aryl, or (C3-C20)heteroaryl, and at least one of the $R_1$ and $R_2$ is fluoro(C1-C20)alkyl, (C6-C20)aryl, or (C3-C20)heteroaryl;

$X_1$ is O or $SO_2$;

$Ar_1$ and $Ar_2$ are independently of each other

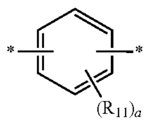

or

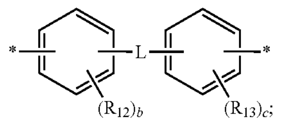

L is a single bond, —O—, —S—, —$SO_2$—, (C1-C7) alkylene, (C6-C12)arylene, or a combination thereof, and the arylene and the alkylene of L may be further substituted by one or more selected from (C1-C7)alkyl and halo(C1-C7)alkyl;

$R_{11}$ to $R_{13}$ are independently of one another (C1-C7)alkyl, (C1-C7)alkoxy, or halo(C1-C7)alkyl; and a to c are independently of one another an integer of 0 to 2.

As an example, in Chemical Formula 5, $R_1$ and $R_2$ may be independently of each other hydrogen, (C1-C7)alkyl, fluoro (C1-C7)alkyl, (C6-C12)aryl, or (C3-C12)heteroaryl, and at least one of the $R_1$ and $R_2$ may be fluoro (C1-C7)alkyl, (C6-C12)aryl, or (C3-C12)heteroaryl.

As an example, in Chemical Formula 5, $R_1$ and $R_2$ may be the same as or different from each other and be fluoro (C1-C20)alkyl, and specifically, may be perfluoro(C1-C20) alkyl or perfluoro(C1-C7)alkyl.

Specifically, the polyamideimide according to an exemplary embodiment may include a repeating unit represented by Chemical Formula 5-1:

[Chemical Formula 5-1]

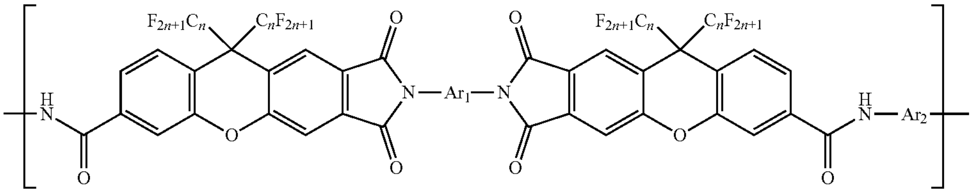

wherein n is an integer of 1 to 5, and $Ar_1$ and $Ar_2$ are as defined above in Chemical Formula 5.

As an example, in Chemical Formula 5, n may be an integer of 1 to 3, or 1 or 2.

Specifically, the polyamideimide according to an exemplary embodiment may include a repeating unit represented by Chemical Formula 6:

[Chemical Formula 6]

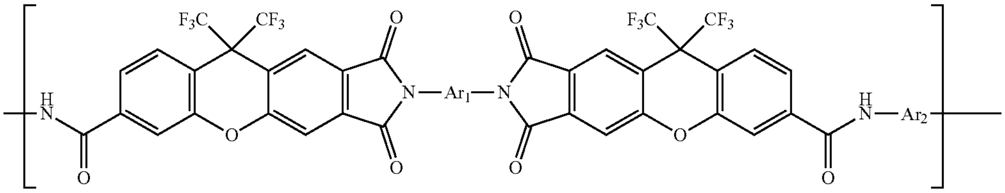

wherein $Ar_1$ and $Ar_2$ are independently of each other

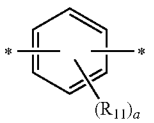

or

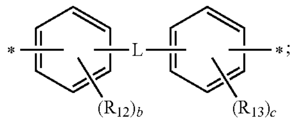

L is a single bond, —O—, —S—, or —$CR_{14}R_{15}$-;

$R_{11}$ to $R_{15}$ are independently of one another (C1-C3)alkyl or fluoro(C1-C3)alkyl; and a to c are independently of one another an integer of 0 to 2.

As an example, $Ar_1$ and $Ar_2$ may be independently of each other selected from the following structures:

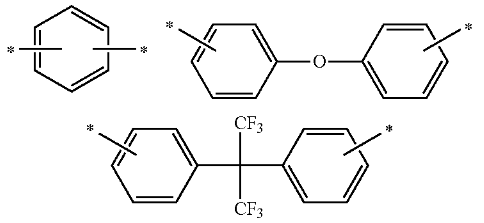

-continued

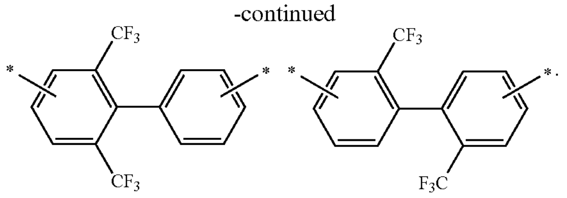

As an example, the polyamideimide according to an exemplary embodiment may include a repeating unit represented by the following Chemical Formula 7 or 8, but is not limited thereto:

[Chemical Formula 7]

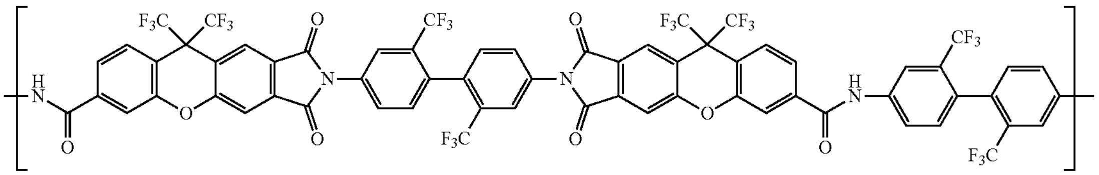

[Chemical Formula 8]

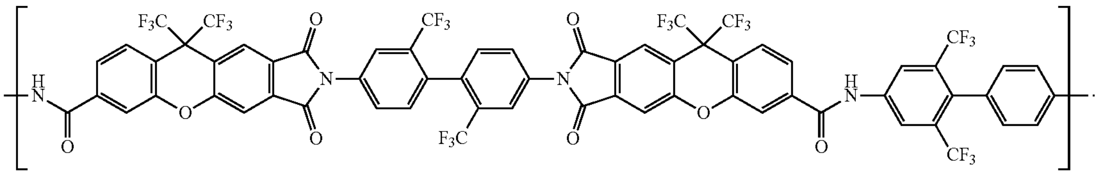

The polyamideimide according to an exemplary embodiment may have a number average molecular weight of 10,000 to 200,000 g/mol, 50,000 to 200,000 g/mol, or 80,000 to 200,000 g/mol.

Hereinafter, a method of producing the polyamideimide according to an exemplary embodiment will be described, but an organic solvent used herein is not limited, and a reaction time and a temperature may also be changed within a range which does not departing from the gist of the invention, of course.

The polyamideimide according to an exemplary embodiment may be produced by including: reacting and imidizing an acid anhydride compound represented by the following Chemical Formula 1 and an aromatic diamine represented by the following Chemical Formula A to produce a dicarboxylic acid compound represented by the following Chemical Formula 4; and reacting the dicarboxylic acid compound represented by Chemical Formula 4 and an aromatic diamine represented by the following Chemical Formula B to produce a polyamideimide including a repeating unit represented by the following Chemical Formula 5:

[Chemical Formula 1]

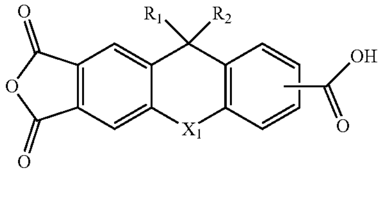

-continued

[Chemical Formula 4]

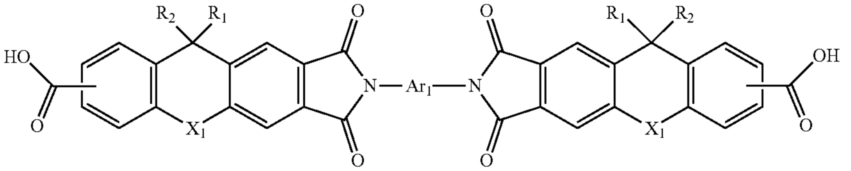

[Chemical Formula 5]

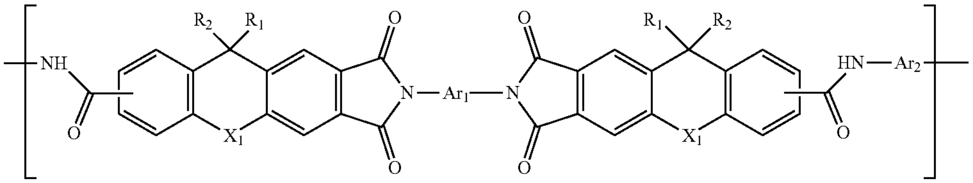

[Chemical Formula A]

$H_2N—Ar_1—NH_2$

[Chemical Formula B]

$H_2N—Ar_2—NH_2$ wherein $R_1$, $R_2$, $X_1$, $Ar_1$, and $Ar_2$ are as defined above in Chemical Formula 5.

Without being bound by a specific theory, as an example, when a step of producing the dicarboxylic acid compound represented by Chemical Formula 4 is not included, regularity (acid anhydride compound-$Ar_1$-acid anhydride compound-$Ar_2$) of a monomer sequence in a polymer chain of the polyamideimide may not be secured and thermal stability of a polyamideimide film is decreased later, so that it may be difficult to implement the physical properties to be desired in the present invention.

Another exemplary embodiment of the present invention provides a composition for forming a polyamideimide film including the polyamideimide.

Specifically, the composition for forming a polyamideimide film according to an exemplary embodiment may include the polyamideimide described above; and an organic solvent.

The organic solvent included in the composition may be one or two or more selected from ketones such as γ-butyrolactone, 1,3-dimethyl-2-imidazolidinone, methyl ethyl ketone, cyclohexanone, cyclopentanone, and 4-hydroxy-4-methyl-2-pentanone; aromatic hydrocarbons such as toluene, xylene, and tetramethylbenzene; glycolethers (cellosolve) such as ethylene glycol monoethyl ether, ethylene glycol monomethyl ether, ethylene glycol monobutyl ether, diethylene glycol monoethylether, diethylene glycol monomethylether, diethylene glycol monobutyl ether, propylene glycol monomethyl ether, propylene glycol monoethyl ether, dipropylene glycol diethyl ether, and triethylene glycol monoethyl ether; acetates such as ethyl acetate, butyl acetate, ethylene glycol monoethyl ether acetate, ethylene glycol monobutyl ether acetate, diethylene glycol monoethyl ether acetate, and dipropylene glycol monomethyl ether acetate; alcohols such as methanol, ethanol, propanol, ethylene glycol, propylene glycol, and carbitol; amides such as N,N-dimethylpropionamide (DMPA), N,N-diethylpropionamide (DEPA), N,N-dimethylacetamide (DMAc), N,N-diethylacetamide (DEAc), N,N-dimethylformamide (DMF), N,N-diethylformamide (DEF), N-methylpyrrolidone (NMP), N-ethylpyrrolidone (NEP), and N,N-dimethylmethoxyacetamide; and the like, but is not limited thereto.

The composition for forming a polyamideimide film according to an exemplary embodiment may have a solid content (polyamideimide polymer) of 5 wt % or more or 10 wt % or more, specifically 5 wt % to 50 wt %, 10 wt % to 40 wt %, or 20 wt % to 40 wt %, based on the total weight of the composition.

Another exemplary embodiment of the present invention provides a polyamideimide film formed from the composition for forming a polyamideimide film.

The polyamideimide film according to an exemplary embodiment may have a thickness of 1 to 500 μm, 1 to 100 μm, 1 to 50 μm, or 1 to 20 μm.

In addition, the polyamideimide film has excellent thermal stability with a glass transition temperature ($T_g$) of 400° C.; or higher, and may have a coefficient of thermal expansion (CTE) of 20 ppm/° C.; or less as measured in a temperature range of 100 to 450° C.; by a thermomechanical analysis (TMA) method.

That is, the polyamideimide film according to an exemplary embodiment is not deformed even in a high temperature process required in a flexible device, and may minimize a difference in expansion and contraction between different types of materials at a high temperature process.

In addition, the polyamideimide film according to an exemplary embodiment may have a yellow index in accordance with ASTM D1925 of 5 or less, 4 or less, or 3 or less.

That is, since the polyamideimide film according to an exemplary embodiment may have high thermal stability and a low coefficient of thermal expansion while being colorless and transparent, it is expected to be applied as a substrate material of a flexible display element involved in a high-temperature process.

Hereinafter, the exemplary embodiments described above will be described in detail through the following examples. However, the following examples are only for description, and do not limit the scope of rights.

[Method of Measuring Physical Properties]

(1) Number Average Molecular Weight

It was measured using gel permeation chromatography (GPC). 10 μm of PLgel MIXED-B as a column, polystyrene as a standard sample, and tetrahydrofuran (THF) as a solvent were used, a sample at a concentration of 5 mg/10 mL was prepared under the conditions of a temperature of 30° C. and a flow rate of 1.0 mL/min and supplied in an amount of 200 μL, and then measurement was performed.

(2) Yellow Index

It was measured according to the ASTM D1925 standard.

(3) Cut-Off Wavelength

A transmittance was measured in accordance with the ASTM D1003 standard, and a wavelength at which the transmittance began to appear was set as a cut-off wavelength (A°) of each film.

(4) Transmittance

A transmittance at a wavelength of 400 nm ($T_{400\ nm}$) and a transmittance at a wavelength of 550 nm ($T_{550\ nm}$) were measured, respectively, in accordance with the ASTM D1003 standard.

(5) Thermal Decomposition Temperature ($T_{d,\ 5\%}$)

A thermogravimetric analysis (TA instruments, TGA Q50) method was used. The measurement was performed in a temperature range from room temperature to 800° C., at a heating rate of 5° C./min, and at a pressure of 1.5 bar/min with a nitrogen gas injection as the measurement conditions, and a temperature at which a mass decrease of 5% occurred was set as a thermal decomposition temperature ($T_{d,\ 5\%}$).

(6) Glass Transition Temperature ($T_g$)

Heating and cooling were performed at 10° C./min from 0° C. to 400° C. using an isothermal differential scanning calorimetry (TA instruments, DSC Q20), and a second value obtained therefrom was used.

(7) Coefficient of Thermal Expansion (CTE)

It was measured using a thermomechanical analyzer (TA instruments, TMA-Q400). The measurement was performed with a load of 0.01 N at a heating rate of 5° C./min in a temperature range from room temperature to 450° C. and the expansion rates were averaged.

(8) Alpha Transition Temperature ($T_\alpha$)

It was measured with a dynamic mechanical analyzer (TA instruments, DMA Q800) in accordance with the ASTM D4065 standard. The alpha transition temperature was measured with a load of 0.01 N under the conditions of a temperature range from room temperature to 450° C., a heating rate of 5° C./min, a frequency of 1 Hz, and an amplitude of 15 μm. Since the glass transition temperature was not observed up to 450° C. in a differential scanning calorimetry, the alpha transition temperature observed at a temperature similar to the glass transition temperature was measured.

[Production Example 1] Production of Acid Anhydride Compound

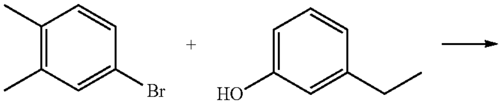

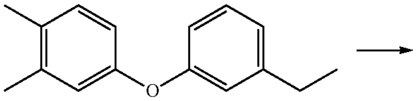

A-1

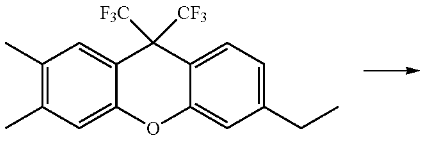

A-2

-continued

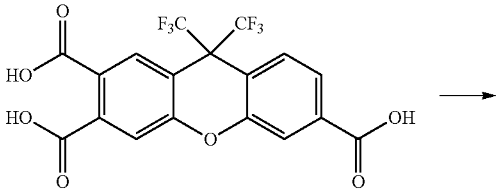

A-3

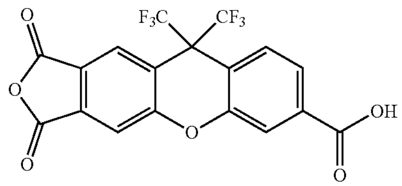

A 7.88 g of 4-bromo-1,2-dimethylbenzene, 4.00 g of 3-ethylphenol, 1.16 g of iron(III) acetylacetonate ($Fe(acac)_3$), 0.62 g of copper iodide (CuI), 9.05 g of potassium carbonate ($K_2CO_3$), and 5 mL of anhydrous dimethylformamide (DMF) were added to a three-neck round bottom flask to produce a reaction solution. The reaction solution was stirred at 135° C. for 12 hours, and then extraction was performed with hexane to obtain Compound A-1.

Compound A-1 was added to a one-neck round bottom flask with 26.45 g of hexafluoroacetone trihydrate in a mixed solvent of 34 mL of dichloromethane (DCM) and 34 mL of triflic acid. Stirring was performed at room temperature for 33 hours, and the reaction solution was slowly added to a sodium hydroxide (NaOH) aqueous solution to perform neutralization. Thereafter, extraction was performed with diethyl ether to obtain a product, the product was stirred once again at room temperature for 20 hours under a mixed solvent of 49.5 mL of dichloromethane (DCM) and 98.9 mL of triflic acid, a reaction solution was slowly added to a sodium hydroxide (NaOH) aqueous solution in the same manner to perform neutralization, and extraction was performed with hexane to obtain Compound A-2.

Compound A-2 was oxidized with sodium hydroxide and potassium permanganate ($KmnO_4$) in a mixed solvent of 243.5 mL of pyridine and 21 mL of distilled water, and then treated with a sulfuric acid aqueous solution at pH 1 to obtain Compound A-3 which was a tricarboxylic acid compound. Compound A-3 was sublimated into vacuum to obtain Compound A (yield: 15%) which was an acid anhydride compound.

$^1$H-NMR (400 MHz, Acetone-$d_6$), δ (ppm): 11.93 (broad, COOH, 1H), 8.53 (s, 1H), 8.17 (d, J=8.6 Hz, 1H), 8.08 (s, 1H), 8.05 (dd, J=8.6, 1.9 Hz, 1H), 7.99 (d, J=1.8 Hz, 1H).

<Production of Polyamideimide Resin>

Example 1

Production of Dicarboxylic Acid Compound

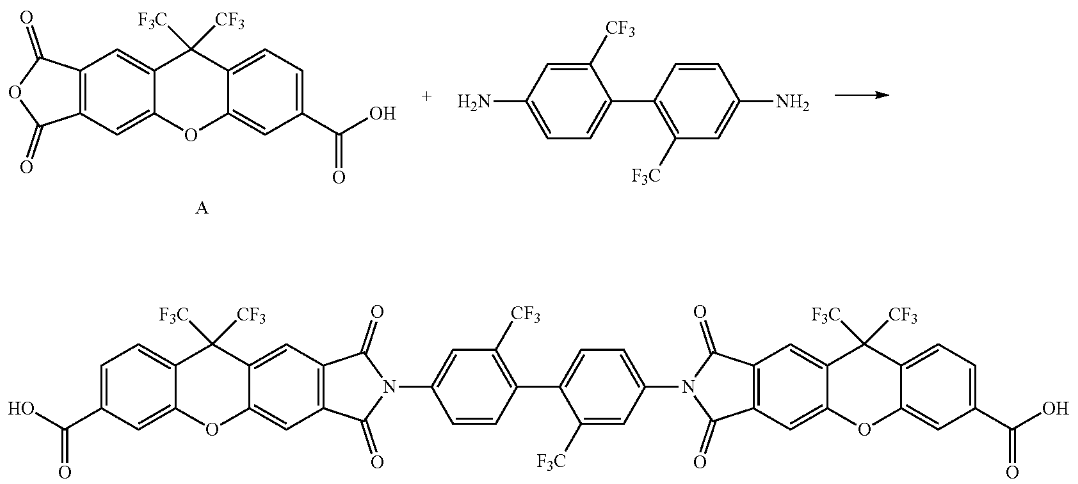

A 8.57 g of Compound A, 3.17 g of 2,2'-bis(trifluoromethyl) benzidine, and 50 mL of dimethylacetamide were added to a round bottom flask, stirring was performed at room temperature for 12 hours while nitrogen was flowed, 5.06 g of acetic anhydride and 5.56 g of DABCO were added, and stirring was further performed for 14 hours. The reaction solution was poured into the aqueous solution at pH 1, and the settled precipitate was dried to produce a dicarboxylic acid compound (yield: 100%).

Production of Polyamideimide Resin

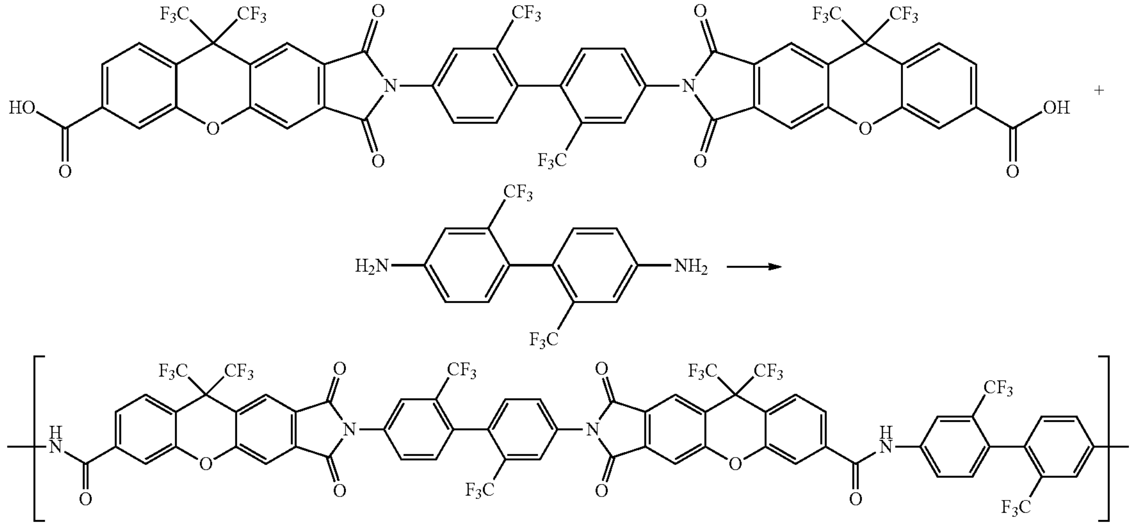

1

379.52 mg (0.33 mmol) of the dicarboxylic acid compound obtained above and 105.70 mg (0.33 mmol) of 2,2'-bis(trifluoromethyl)benzidine (TFMB) were added to a three-neck round bottom flask, and 0.3 g of calcium chloride ($CaCl_2$)), 1 mL of triphenylphosphite (TPP), 1 mL of pyridine, and 5 mL of anhydrous N-methylpyrrolidone were added thereto to prepare a reaction solution. The flask was equipped with a nitrogen inlet and outlet and a mechanical stirrer, and the reaction solution was stirred at 100° C. for 8 hours. After the reaction was completed, the reaction solution was precipitated in a solution having a volume ratio of water to methanol of 1:1, and the precipitated polymer was washed several times with methanol after filtration and then dried in a vacuum oven at 80° C. The dried polymer was dissolved in dimethylacetamide again, precipitated in methanol, filtered, and dried in a vacuum oven at 180° C. to obtain the polyamideimide resin 1 of Example 1 (yield: 100%). The number average molecular weight of the polyamideimide resin of Example 1 was 94,400 g/mol.

$^1$H-NMR (DMF-$d_7$, 400 MHz), δ (ppm): 11.31 (s, amide, 1H), 10.83 (s, amide, 1H), 8.81 (s, 2H), 8.44 (s, 2H), 8.33-8.21 (m, 4H), 8.28 (s, 2H), 8.18-8.16 (m, 6H), 8.08 (d, J=7.7 Hz, 2H), 7.85 (d, J=8.6 Hz, 2H), 7.47 (d, J=8.9 Hz, 2H).

Example 2

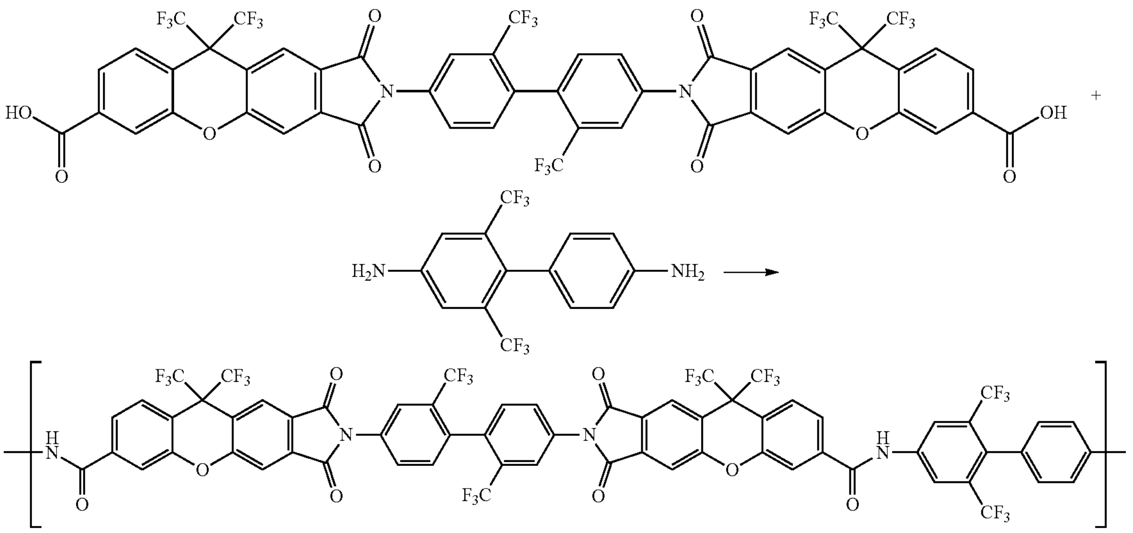

2

The polyamideimide resin of Example 2 was produced (yield: 100%) in the same manner as in Example 1, except that 2,6-bis(trifluoromethyl)benzidine was used instead of 2,2'-bis(trifluoromethyl)benzidine (TFMB) in the step of producing the polyamideimide resin. The 2,6-bis(trifluoromethyl)benzidine was produced by a method known in Korean Patent Laid-Open Publication No. 10-2014-0085064, and the number average molecular weight of the polyamideimide resin of Example 2 was 104,900 g/mol.

$^1$H-NMR (DMF-$d_7$, 400 MHz), δ (ppm): 11.31 (s, amide, 1H), 10.83 (s, amide, 1H), 8.81 (s, 2H), 8.44 (s, 2H), 8.33-8.21 (m, 4H), 8.28 (s, 2H), 8.18-8.16 (m, 6H), 8.08 (d, J=7.7 Hz, 2H), 7.85 (d, J=8.6 Hz, 2H), 7.47 (d, J=8.9 Hz, 2H).

<Production of Polyamideimide Film>

Each of the polyamideimide resins of Examples 1 and 2 produced above was dissolved at 35 wt % in N,N'-dimethylacetamide (DMAc) to produce a composition for forming a polyamideimide film. The composition was drop cast on a glass substrate, dried at 30° C. for 12 hours, heat-treated at 200° C. for 6 hours, and cooled to room temperature. Thereafter, the film formed on the glass substrate was separated from the substrate to obtain a polyamideimide film having a thickness of about 10 μm. The physical properties of the polyamideimide film were measured by the method described in the method of measuring physical properties, and the results are shown in the following Table 1:

As shown in Table 1, it was confirmed that the polyamideimide film produced from the novel acid anhydride compound according to an exemplary embodiment had a high transmittance to a wavelength in a visible light region and a low yellow index, and transmitted light in a wide wavelength region. In addition, since the polyamideimide film according to an exemplary embodiment had a high thermal decomposition temperature both in nitrogen conditions and air conditions, it had excellent thermal stability without environmental influence, and it is shown that the film had a low coefficient of thermal expansion of 20 ppm/° C. or less. That is, the polyamideimide film according to an exemplary embodiment was not only colorless and transparent, but also not deformed even in a high-temperature process and was able to minimize a difference of expansion and contraction between different types of materials. Thus, it is expected to be usefully applied as a substrate of a flexible display element.

The novel acid anhydride compound according to an exemplary embodiment may provide a polyamideimide film having both excellent thermal properties and excellent optical properties. Specifically, the polyamideimide film produced from the novel acid anhydride compound according to an exemplary embodiment may be colorless and transparent, and may also have a high glass transition temperature of 400° C. or higher and a low coefficient of thermal expansion of 20 ppm/° C.; or less.

That is, the polyamideimide film according to an exemplary embodiment is expected to be applied as a substrate material of a flexible display element involved in a high-temperature process.

TABLE 1

| | $\lambda^0$ | Transmittance (%) | | $T_{d,5\%}$ (° C.) | | $T_g$ (° C.) | CTE (ppm/° C.) | | Yellow | |
|---|---|---|---|---|---|---|---|---|---|---|
| | (nm) | $T_{400\,nm}$ | $T_{550\,nm}$ | In $N_2$ | In air | (Tα) | $2^{nd}$ run | $3^{rd}$ run | index | Mn |
| Example 1 | 340 | 83.1 | 88.7 | 487 | 478 | >400 | 14.7 | 14.9 | 2.48 | 94,400 |
| Example 2 | 338 | 85.5 | 88.9 | 488 | 479 | >400 | 16.9 | 17.2 | 1.83 | 104,900 |

Hereinabove, although the present invention has been described by specified matters and specific exemplary embodiments, they have been provided only for assisting in the entire understanding of the present invention. Therefore, the present invention is not by the specific matters limited to the exemplary embodiments. Various modifications and changes may be made by those skilled in the art to which the present invention pertains from this description.

Therefore, the spirit of the present invention should not be limited to the above-described exemplary embodiments, and the following claims as well as all modifications equal or equivalent to the claims are intended to fall within the scope and spirit of the invention.

What is claimed is:

1. A polyamideimide comprising: a structural unit derived from an acid anhydride compound represented by the following Chemical Formula 1 and a structural unit derived from an aromatic diamine:

[Chemical Formula 1]

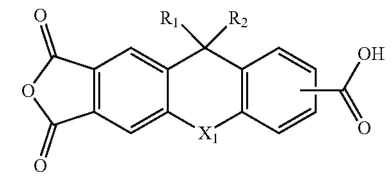

wherein $R_1$, $R_2$, are independently of each other hydrogen, $(C_1\text{-}C_{20})$alkyl, fluoro$(C_1\text{-}C_{20})$alkyl, $(C_6\text{-}C_{20})$aryl, or $(C_3\text{-}C_{20})$ heteroaryl, and at least one of $R_1$ and $R_2$ is fluoro $(C_1\text{-}C_{20})$alkyl, $(C_6\text{-}C_{20})$aryl or $(C_3\text{-}C_{20})$ heteroaryl and $X_1$ is O or $SO_2$.

2. The polyamideimide of claim 1, wherein the polyamideimide includes a repeating unit represented by the following Chemical Formula 5:

[Chemical Formula 5]

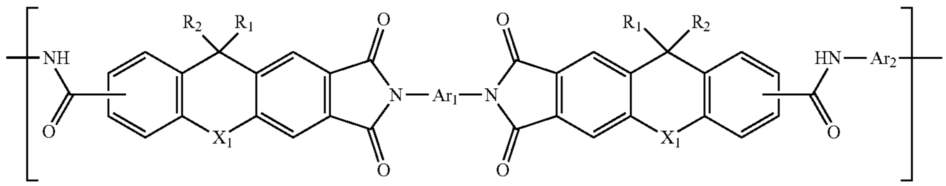

wherein $R_1$ and $R_2$ are independently of each other hydrogen, (C1-C20)alkyl, fluoro (C1-C20)alkyl, (C6-C20)aryl, or (C3-C20) heteroaryl, and at least one of the $R_1$ and $R_2$ is fluoro (C1-C20)alkyl, (C6-C20)aryl, or (C3-C20) heteroaryl;

$X_1$ is O or $SO_2$;

$Ar_1$ and $Ar_2$ are independently of each other

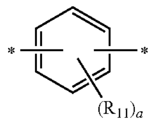 or 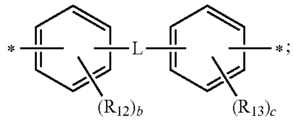;

L is a single bond, —O—, —S—, —$SO_2$—, (C1-C7) alkylene, (C6-C12)arylene, or a combination thereof, and the arylene and the alkylene of L may be further substituted by one or more selected from (C1-C7)alkyl and halo(C1-C7)alkyl;

$R_{11}$ to $R_{13}$ are independently of one another (C1-C7)alkyl, (C1-C7)alkoxy, or halo(C1-C7)alkyl; and a to c are independently of one another an integer of 0 to 2.

3. The polyamideimide of claim 2, wherein the polyamideimide includes a repeating unit represented by the following Chemical Formula 6:

[Chemical Formula 6]

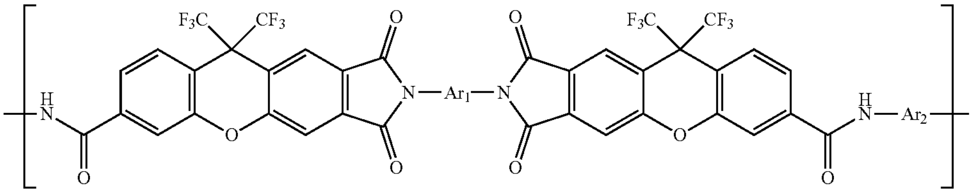

wherein $Ar_1$ and $Ar_2$ are independently of each other

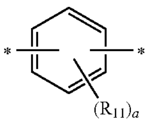 or 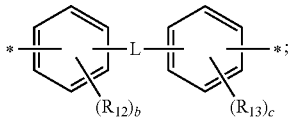;

L is a single bond, —O—, —S—, or —$CR_{14}R_{15}$—;

$R_{11}$ to $R_{15}$ are independently of one another (C1-C3)alkyl or fluoro (C1-C3)alkyl; and a to c are independently of one another an integer of 0 to 2.

4. The polyamideimide of claim 3, wherein $Ar_1$ and $Ar_2$ are independently of each other selected from the following structures:

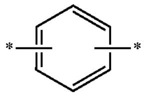

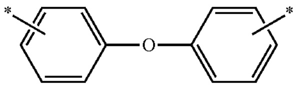

-continued

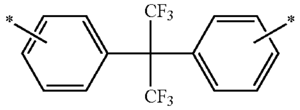

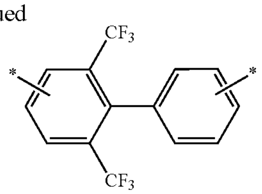

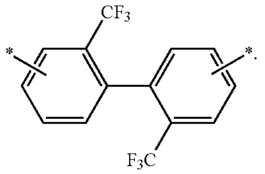.

5. The polyamideimide of claim 4, wherein the polyamideimide includes a repeating unit represented by the following Chemical Formula 7 or 8:

[Chemical Formula 7]

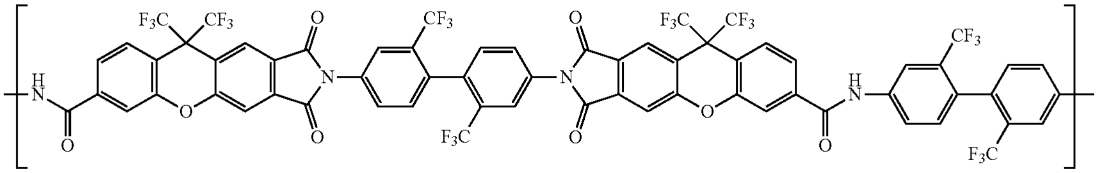

[Chemical Formula 8]

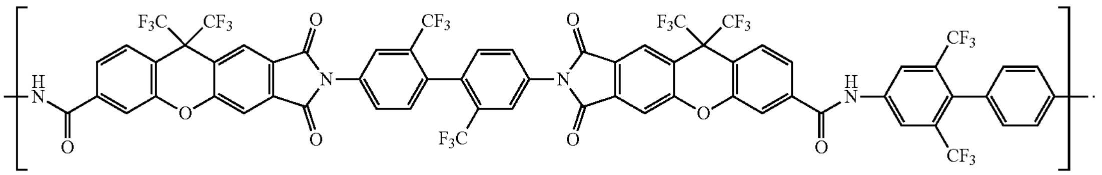.

6. The polyamideimide of claim 5, wherein the polyamideimide has a number average molecular weight of 10,000 to 200,000 g/mol.

7. A composition for forming a polyamideimide film comprising the polyamideimide of claim 1.

8. A polyamideimide film formed from the composition for forming a polyamideimide film of claim 7.

9. The polyamideimide film of claim 8, wherein the polyamideimide film has a thickness of 1 to 20 μm and a glass transition temperature ($T_g$) of 400° C. or higher.

10. The polyamideimide film of claim 9, wherein the polyamideimide film has a coefficient of thermal expansion (CTE) of 20 ppm/° C. or less as measured in a temperature range of 100 to 450° C. by a thermomechanical analysis (TMA) method.

11. The polyamideimide film of claim 10, wherein the polyamideimide film has a yellow index in accordance with ASTM D1925 of 4 or less.

* * * * *